United States Patent [19]

Tsuchida et al.

[11] Patent Number: 5,484,714
[45] Date of Patent: Jan. 16, 1996

[54] METHOD OF PRODUCING TREHALOSE BY MICROORGANISMS WHICH CAN PRODUCE TREMALOSE WITH SUCROSE OR MALTOSE AS MAIN CARBON SOURCE

[75] Inventors: Takayasu Tsuchida; Yutaka Murakami; Yoshitaka Nishimoto; Takuya Kotani, all of Kawasaki, Japan

[73] Assignee: Ajinomoto Co., Inc., Tokyo, Japan

[21] Appl. No.: 989,385

[22] Filed: Dec. 11, 1992

[30]    Foreign Application Priority Data

Dec. 11, 1991  [JP]  Japan ..................... 3-327494
Feb. 13, 1992  [JP]  Japan ..................... 4-026841

[51] Int. Cl.$^6$ .................. C12P 19/12; C12N 1/12; C12N 1/20
[52] U.S. Cl. ............ 435/100; 435/252.1; 435/822; 435/830; 435/840; 435/843
[58] Field of Search ............... 435/100, 252.32, 435/252.1, 822, 830, 840, 843

[56]    References Cited

U.S. PATENT DOCUMENTS

| | | | |
|---|---|---|---|
| 3,639,210 | 2/1972 | Tanaka et al. | 195/28 R |
| 3,655,512 | 4/1972 | Tanaka et al. | 195/28 R |
| 5,006,514 | 4/1991 | Kato et al. | 514/53 |
| 5,169,767 | 12/1992 | Matsuura et al. | 435/100 |
| 5,336,617 | 8/1994 | Sugitani et al. | 435/252.1 |
| 5,403,727 | 4/1995 | Miwa et al. | 435/100 |

FOREIGN PATENT DOCUMENTS

| | | |
|---|---|---|
| 0555540 | 8/1993 | European Pat. Off. . |
| 2671099 | 7/1992 | France . |
| 1642708 | 3/1974 | Germany . |
| 50-154485 | 12/1975 | Japan . |
| 0216695 | 12/1983 | Japan . |
| 3160995 | 7/1991 | Japan . |
| 3180172 | 8/1991 | Japan . |

OTHER PUBLICATIONS

Chemical Abstracts, vol. 103, No. 17, Oct. 28, 1985, AN 138281u.
Kunugita, K. et al, Translation of Japanese Kokai 50–154485.

*Primary Examiner*—Marian C. Knode
*Assistant Examiner*—K. Larson
*Attorney, Agent, or Firm*—Oblon, Spivak, McClelland, Maier, & Neustadt

[57]    ABSTRACT

A method of producing trehalose, in which a microorganism belonging to the genus Brevibacterium, Corynebacterium, Microbacterium or Arthrobacter and having the ability to produce trehalose is incubated in a liquid medium containing sucrose or maltose as an essential carbon source and the trehalose produced and accumulated in the culture is collected therefrom. Trehalose is produced inexpensively and efficiently by industrial mass-production.

5 Claims, No Drawings

METHOD OF PRODUCING TREHALOSE BY MICROORGANISMS WHICH CAN PRODUCE TREMALOSE WITH SUCROSE OR MALTOSE AS MAIN CARBON SOURCE

BACKGROUND OF THE INVENTION

1. Field of the Invention

The present invention relates to a method of producing trehalose; α-D-glucopyranosyl-α-D-glucopyranoside. Trehalose can be used as a cell activity-retaining agent, a cold-resistant agent and an anti-freezing agent in the field of medicines and foods.

2. Discussion of the Background:

Known methods for producing trehalose include extracting it from natural substances such as Selaginella or dry yeast, a method of incubating a microorganism belonging to the genus Arthrobacter with n-alkanes as carbon sources (Agric. Biol. Chem., Vol. 33, pages 190 to 195, 1969), and a method of using a microorganism belonging to the genus Nocardia (Japanese Patent Application Laid-Open No. 50-154485). However, these are not suitable for industrial mass-production of trehalose in view of the cost and the efficiency.

SUMMARY OF THE INVENTION

Accordingly, one object of this invention is to provide a method of producing trehalose inexpensively and efficiently by industrial mass-production in which a microorganism belonging to the genus Brevibacterium, Corynebacterium, Microbacterium or Arthrobacter having the ability to produce trehalose is incubated in a liquid medium containing sucrose or maltose as an essential carbon source, and the trehalose accumulated in the culture is collected therefrom.

Another object of the invention is to provide a method of producing trehalose in which the osmotic pressure of the culture medium is 1671–3974 mmol/kg.

DETAILED DESCRIPTION OF THE PREFERRED EMBODIMENTS

The present inventors earnestly and repeatedly studied for the purpose of developing a method of producing trehalose inexpensively and efficiently by industrial mass-production and, as a result, have found that when microorganisms belonging to the genera Brevibacterium, Corynebacterium, Microbacterium and Arthrobacter, which have heretofore been known as microorganisms which produce L-glutamic acid and various other amino acids, are cultured in a liquid medium containing sucrose or maltose as an essential carbon source, then a noticeable amount of trehalose is produced and accumulated in the culture medium. Furthermore, when the osmotic pressure of the liquid medium is defined to fall within the range of from 1671 to 3974 mmol/kg, the amount of trehalose produced and accumulated increases noticeably. On the basis of these findings, they have completed the present invention.

Specifically, the present invention provides a method of producing trehalose in which a microorganism belonging to the genus Brevibacterium, Corynebacterium, Microbacterium or Arthrobacter is incubated in a liquid medium containing sucrose or maltose as an essential carbon source. The trehalose produced and accumulated in the culture medium is collected therefrom. The present invention further provides a method of producing trehalose in which a microorganism belonging to the genus Brevibacterium, Corynebacterium, microbacterium or Arthrobacter and having an ability of producing trehalose is incubated in a liquid medium containing sucrose or maltose as an essential carbon source and having an osmotic pressure of from 1671 to 3974 mmol/kg and the trehalose as produced and accumulated in the culture is collected therefrom.

The microorganisms to be used in the present invention may be those of any strain belonging to the genus Brevibacterium, Corynebacterium, Microbacterium or Arthrobacter and having the ability to produce trehalose. The following strains are suitable.

*Brevibacterium lactofermentum* ATCC 13869
*Brevibacterium flavum* ATCC 14067
*Brevibacterium divaricatum* ATCC 21642
*Corynebacterium glutamicum* ATCC 13032
*Corynebacterium acetoacidophilum* ATCC 13870
*Corynebacterium lilium* ATCC 15990
*Arthrobacter citreus* ATCC 11624
*Arthrobacter sulfreus* ATCC 15170
*Microbacterium ammoniaphilum* ATCC 15354

Mutants of these strains derived by conventional mutagenesis techniques, such as treatment with ultraviolet light or an N-nitrosamine, so as to augment the trehalose-producing ability, may also be used in the present invention.

An important aspect of the present invention is that incubation of the cells of the microorganism is conducted in a liquid medium containing sucrose or maltose as an essential carbon source. Glucose is used in conventional media as a raw material for fermentation of amino acids. In the method of producing trehalose according to the present invention, however, the cells of suitable strains are incubated with an essential carbon source of sucrose or maltose whereby a much larger amount of trehalose is produced than when using glucose as an essential carbon source. Where sucrose is used as an essential carbon source, a substance having a high sucrose content, such as beet molasses may also be used, naturally. By defining the osmotic pressure of the liquid medium to fall within the range of from 1671 to 3974 mmol/kg, the amount of trehalose produced and accumulated is noticeably elevated to give a more favorable result.

Components other than the carbon source used in the liquid medium include nitrogen sources, inorganic salts and organic minor nutrients. Usable nitrogen sources, for example, are ammonium salts, aqueous ammonia, urea as well as corn steep liquor, protein hydrolysates and amino acid mixtures. Suitable inorganic salts include, for example, phosphates and magnesium salts. Organic minor nutrients include, for example, suitable amounts of thiamine and biotin. Antibiotics such as penicillin and surfactants such as polyoxysorbitan monopalmitate may be added to the medium initially or during the course of incubation, whereby the amount of trehalose produced and accumulated may often be elevated.

The osmotic pressure of the liquid medium is preferably from 1671 to 3974 mmol/kg but is not strictly limited to that range. For instance, there is mentioned a method of adding a salt such as potassium chloride, sodium chloride, ammonium chloride, potassium sulfate or sodium sulfate to the medium in an amount of approximately from 0.5 to 7%.

Incubation is preferably effected under aerobic conditions, the incubating temperature is preferably from 20° to 45° C., and the pH value of the culture is preferably controlled to fall within the range of from 5.0 to 10.0. For adjustment of the pH value, inorganic or organic acidic or alkaline substances are usable, such as urea, calcium carbonate and ammonia gas.

For collecting trehalose from the culture after incubation, any known method, such as ion exchange resin methods, resin chromatographic methods or ethanol crystallization methods may be employed singly or in combination.

Other features of the invention will become apparent in the course of the following descriptions of exemplary embodiments which are given for illustration of the invention and are not intended to be limiting thereof.

Determination of trehalose was effected by high performance liquid chromatography using a column containing PA-03-S-5 manufactured by YMC.

EXAMPLE 1

A liquid medium containing 10% of the saccharide as shown in Table 1 below as a carbon source and comprising 2% of ammonium sulfate, 0.1% of $KH_2PO_4$, 0.1% of $MgSO_4 7H_2O$, 200 µg/l of thiamine hydrochloride, 5 µg/liter of biotin, 0.036% (as total nitrogens) of concentrated soybean decomposate liquid, 0.001% of $FeSO_4 7H_2O$ and 0.001% of $MnSO_4 4H_2O$ (pH 7.0) was prepared. This was put in plural 500 ml-shaking flasks in an amount of 20 ml each and sterilized under heat at 115° C. for 10 minutes. To the medium was added 50% of calcium carbonate sterilized under dry heat. Cells of *Brevibacterium lactofermentum* ATCC 13869, *Brevibacterium flavum* ATCC 14067 or *Corynebacterium lilium* ATCC 15990, previously cultivated on a bouillon-agar slant medium at 30° C. for 24 hours, were inoculated to the medium each in an amount of one platinum loop for each flask, and incubation of the cells was effected at 31.5° C. in a back-and-forth shaking incubator. The incubation was finished in 48 hours, and the amount of trehalose as produced and accumulated in the culture was determined.

EXAMPLE 2

A liquid medium containing 10% of the saccharide as shown in Table 2 below as a carbon source and comprising 2% of ammonium sulfate, 0.1% of $KH_2PO_4$, 0.1% of $MgSO_4 7H_2O$, 100 µg/liter of thiamine hydrochloride, 100 µg/liter of biotin, 0.036% (as total nitrogens) of concentrated soybean decomposate liquid, 0.001% of $FeSO_4.7H_2O$ and 0.001% of $MnSO_4.4H_2O$ (pH 7.0) was prepared. This was put in plural 500 ml-shaking flasks in an amount of 20 ml each and sterilized under heat at 115° C. for 10 minutes. To the medium was added 50% of calcium carbonate as sterilized under dry heat. Cells of *Microbacterium ammoniaphilum* ATCC 15354 or *Arthrobacter sulfreus* ATCC 15170, as previously cultivated on a bouillonagar slant medium at 30° C. for 24 hours, were inoculated to the medium each in an amount of one platinum loop for each flask, and incubation of the cells was effected at 31.5° C. in a back-and-forth shaking incubator. Polyoxysorbitan monopalmitate was added to each flask, at the point when the absorbance of the 1/26 diluted liquid of the culture at 562 nm became 0.6 after initiation of incubation, to have a concentration of 0.4% and the incubation was continued further. The incubation was finished in 48 hours, and the amount of trehalose as produced and accumulated in the culture was determined. The results are shown in Table 2 below.

TABLE 1

| Microorganisms Used | Carbon Sources | | | |
|---|---|---|---|---|
| | Glucose | Sucrose | Maltose | Beet Molasses |
| B. lactofermentum ATCC13869 | 0.02 | 1.25 | 0.83 | 0.90 |
| B. flavum ATCC14067 | 0.01 | 0.86 | 0.74 | 0.70 |
| C. lilium ATCC15990 | 0.01 | 0.77 | 0.73 | 0.61 |

The numerical value of Table 1 indicates the amount of trehalose accumulated (g/dl) in the culture.

Where beet molasses was used as a carbon source, polyoxysorbitan monopalmitate was added to the medium, at the point when the absorbance of the 1/26 diluted liquid of the culture at 562 nm became 0.6 after initiation of incubation, to have a concentration of 0.4%, and the incubation was continued further.

As is noted from the results in Table 1 above, incubation of the microorganisms in a medium containing sucrose or maltose yielded a significantly larger amount of trehalose than when cultured in a medium containing glucose.

TABLE 2

| Microorganisms Used | Carbon Sources | | | |
|---|---|---|---|---|
| | Glucose | Sucrose | Maltose | Beet Molasses |
| M. ammoniaphilum ATCC15354 | 0.01 | 0.84 | 0.64 | 0.78 |
| A. sulfreus ATCC15170 | 0.01 | 0.80 | 0.72 | 0.81 |

The numerical value of Table 2 indicates the amount of trehalose accumulated (g/dl) in the culture.

As is noted from the results in Table 2 above, incubation of the microorganisms in a medium containing sucrose or maltose yielded a noticeably large amount of trehalose in the culture.

EXAMPLE 3

A liquid medium comprising 4% of glucose, 0.5% of urea, 0.1% of $KH_2PO_4$, 0.04% of $MgSO_4 7H_2O$, 300 μg/liter of thiamine hydrochloride, 300 μg/liter of biotin, 0.1% (as total nitrogens) of concentrated soybean decomposate liquid, 0.001% of $FeSO_4 7H_2O$ and 0.001% of $MnSO_4.4H_2O$ (pH 6.5) was prepared. This was put in plural 500 ml-shaking flasks in an amount of 20 ml each and sterilized under heat at 110° C. for 10 minutes. Cells of microorganisms shown in Tables 3–8, as previously cultivated on a bouillon-agar slant medium at 31.5° C. for 48 hours, were inoculated to the medium in an amount of one platinum loop for each flask, and incubation of the cells was effected at 31.5° C. for 24 hours in a back-and-forth shaking incubator to prepare a seed culture.

The salts indicated in Tables 3–8 below were added in the amounts indicated therein to a medium (pH 7.3) comprising 15% of sucrose, 0.1% of $KH_2PO_4$, 0.1% of $MgSO_4 7H_2O$, 300 μg/liter of thiamine hydrochloride, 300 μg/liter of biotin, 0.05% (as total nitrogens) of concentrated soybean decomposate liquid, 0.001% of $FeSO_4.7H_2O$ and 0.001% of $MnSO_4 4H_2O$ to prepare a liquid medium. This medium was put in plural one liter-jars fermented and sterilized under heat at 120° C. for 20 minutes. To each of them was inoculated 15 ml of the previously prepared seed culture, which was then cultured at 31.5° C. while introducing air thereinto at a flow rate of ½ vvm stirring at a rate of 700 rpm. The osmotic pressure of the medium at the start of the incubation was measured with a 5100C-Vapor Pressure Osmometer (manufactured by Wescor Co.). During the incubation, the pH of the medium was controlled with ammonia gas to have pH of 7.3. Polyoxysorbitan monopalmitate was added to the medium at the point when the turbidity of the 1/26 diluted liquid of the culture at 562 nm reached 0.60 after the start of the cultivation, to have a concentration of 0.4% and the cultivation was continued further. At the point when the sucrose in the culture was consumed completely, the cultivation was terminated.

TABLE 3

| Microorganisms | Concentration of Potassium Chloride Added (%) | | | | |
|---|---|---|---|---|---|
| | 0 (1545) | 0.5 (1671) | 1.5 (1924) | 3.0 (2304) | 5.0 (2810) |
| B. lactofermentum ATCC13869 | 2.2 | 3.1 | 4.0 | 4.3 | 3.2 |
| C. glutamicum ATCC13032 | 1.8 | 2.5 | 3.0 | 3.2 | 2.7 |
| A. citreus ATCC11624 | 1.2 | 1.8 | 2.0 | 2.8 | 1.9 |
| M. ammoniaphilum ATCC15354 | 1.5 | 2.0 | 2.8 | 2.9 | 2.0 |

The numerical Value as parenthesized indicates the osmotic pressure (mmol/kg) of the medium.
The numerical value in the Table indicates the amount of trehalose accumulated (g/dl).

TABLE 4

| Microorganisms | Concentration of Sodium Chloride Added (%) | | | | |
|---|---|---|---|---|---|
| | 0 (1545) | 0.5 (1690) | 1.0 (1835) | 2.0 (2125) | 4.0 (2705) |
| B. divaricatum ATCC21642 | 1.6 | 2.3 | 3.0 | 3.2 | 2.3 |
| C. lilium ATCC15990 | 1.8 | 2.6 | 3.0 | 3.0 | 2.7 |
| A. citreus ATCC11624 | 1.2 | 1.9 | 2.2 | 2.4 | 2.0 |
| M. ammoniaphilum ATCC15354 | 1.5 | 2.4 | 2.8 | 2.9 | 2.4 |

The numerical value as parenthesized indicates the osmotic pressure (mmol/kg) of the medium.
The numerical value in the Table indicates the amount of trehalose accumulated (g/liter).

TABLE 5

| Microorganisms | Concentration of Ammonium Chloride Added (%) | | | | |
|---|---|---|---|---|---|
| | 0 (1545) | 0.5 (1691) | 1.0 (1837) | 2.0 (2129) | 4.0 (2713) |
| B. lactofermentum ATCC13869 | 2.2 | 3.0 | 3.9 | 3.9 | 3.1 |
| C. glutamicum ATCC13032 | 1.8 | 2.4 | 3.2 | 3.3 | 2.4 |
| A. citreus ATCC11624 | 1.2 | 1.9 | 2.1 | 2.6 | 1.9 |
| M. ammoniaphilum ATCC5354 | 1.5 | 2.3 | 2.7 | 2.7 | 2.4 |

The numerical value as parenthesized indicates the osmotic pressure (mmol/kg) of the medium.
The numerical value in the Table indicates the amount of trehalose accumulated (g/dl).

TABLE 6

| Microorganisms | Concentration of Potassium Sulfate Added (%) | | | | |
|---|---|---|---|---|---|
| | 0 (1545) | 0.5 (1711) | 1.0 (2044) | 3.0 (2544) | 7.0 (3876) |
| B. lactofermentum ATCC13869 | 2.2 | 2.9 | 3.1 | 3.6 | 3.0 |
| C. glutamicum ATCC13032 | 1.8 | 2.4 | 2.8 | 3.2 | 2.9 |
| M. ammoniaphilum ATCC15354 | 1.5 | 1.9 | 2.0 | 3.0 | 2.8 |

The numerical value as parenthesized indicates the osmotic pressure (mmol/kg) of the medium.
The numerical value in the Table indicates the amount of trehalose accumulated (g/dl).

TABLE 7

| Microorganisms | Concentration of Sodium Sulfate Added (%) | | | | |
|---|---|---|---|---|---|
| | 0 (1545) | 0.5 (1718) | 1.5 (2065) | 3.0 (2568) | 7.0 (3974) |
| B. lactofermentum ATCC13869 | 2.2 | 2.8 | 3.1 | 3.5 | 2.9 |
| C. glutamicum | 1.8 | 2.4 | 2.9 | 3.2 | 2.5 |

TABLE 7-continued

| Microorganisms | Concentration of Sodium Sulfate Added (%) | | | | |
|---|---|---|---|---|---|
| | 0 (1545) | 0.5 (1718) | 1.5 (2065) | 3.0 (2568) | 7.0 (3974) |
| ATCC13032 | | | | | |
| M. ammoniaphilum ATCC15354 | 1.5 | 1.9 | 2.1 | 3.0 | 2.0 |

The numerical value as parenthesized indicates the osmotic pressure (mmol/kg) of the medium.
The numerical value in the Table indicates the amount of trehalose accumulated (g/dl).

TABLE 8

| Microorganisms | Concentration of Potassium Chloride/Ammonium Chloride (1/1) Mixture Added (%) | | | | |
|---|---|---|---|---|---|
| | 0 (1545) | 0.5 (1681) | 1.5 (1953) | 2.0 (2089) | 4.0 (2633) |
| B. lactofermentum ATCC13869 | 2.2 | 3.2 | 4.0 | 4.1 | 3.2 |
| C. glutamicum ATCC13032 | 1.8 | 2.6 | 3.0 | 3.8 | 2.7 |
| M. ammoniaphilum ATCC15354 | 1.5 | 2.0 | 2.5 | 3.0 | 2.3 |

The numerical value as parenthesized indicates the osmotic pressure (mmol/kg) of the medium.
The numerical value in the Table indicates the amount of trehalose accumulated (g/dl).

From measurements of the osmotic pressure of the medium and the amount of trehalose accumulated in the culture, it is clear that when the incubation is effected in a medium controlled to have an osmotic pressure falling within the range from 1671 to 3974 mmol/kg due to addition of a salt thereto, then the amount of trehalose produced and accumulated in the medium is noticeably elevated.

EXAMPLE 4

Incubation of *Brevibacterium lactofermentum* ATCC 13869 was effected in the same manner as in Example 1, except that sucrose was used as the carbon source. One liter of the culture obtained was sterilized, then treated with an anion exchange resin AMBERLITE IR-4B and a cation exchange resin AMBERLITE IR-120 and decolored with active charcoal. Next, the decolored liquid was concentrated to about 25 ml, and 75 ml of ethanol was added thereto and left to cool to 5° C. to obtain 8.5 g of trehalose crystals having a purity of 99%.

Obviously, numerous modifications and variations of the present invention are possible in light of the above teachings. It is therefor to be understood that within the scope of the appended claims, the invention may be practiced otherwise than as specifically described herein.

What is claimed as new and desired to be secured by Letter Patent of the United States is:

1. A method of producing trehalose comprising: culturing in a nutrient medium comprising sucrose or maltose as a main carbon source for a time and under conditions to produce trehalose, a microorganism belonging to the genus Brevibacterium or Corynebacterium, or a species selected from the group consisting of *Arthrobacter citreus, Arthrobacter sulfreus* and *Microbacterium ammoniaphilum*, said microorganism having an ability to produce trehalose in a nutrient medium containing sucrose or maltose as the main carbon source, and recovering said trehalose.

2. The method of claim 1, wherein said microorganism is selected from the group consisting of *Brevibacterium lactofermentum* ATCC 13869, *Brevibacterium flavum* ATCC 14067, *Brevibacterium divaricatum* ATCC 21642, *Corynebacterium glutamicum* ATCC 13032, *Corynebacterium acetoacidophilum* ATCC 13870, *Corynebacterium lilium* ATCC 15990, *Arthrobacter citreus* ATCC 11624, *Arthrobacter sulfreus* ATCC 15170, *Microbacterium ammoniaphilum* ATCC 15354.

3. The method of producing trehalose as claimed in claim 1, wherein the osmotic pressure of the liquid medium is from 1671 to 3974 mmol/kg.

4. The method of claim 2, wherein the osmotic pressure of the liquid medium is from 1671 to 3974 mmol/kg.

5. The method of claim 1, wherein said main carbon source is sucrose, and said microorganism is selected from the group consisting of *Brevibacterium lactofermentum* ATCC 13869, *Brevibacterium flavum* ATCC 14067, *Brevibacterium divaricatum* ATCC 21642, *Corynebacterium glutamicum* ATCC 13032, *Corynebacterium acetoacidophilum* ATCC 13870, *Corynebacterium lilium* ATCC 15990, *Arthrobacter citreus* ATCC 11624, *Arthrobacter sulfreus* ATCC 15170, *Microbacterium ammoniaphilum* ATCC 15354.

* * * * *